(12) United States Patent
Hall et al.

(10) Patent No.: US 6,301,972 B1
(45) Date of Patent: Oct. 16, 2001

(54) SUBSTANTIALLY FRICTIONLESS BEARING DEVICE FOR SUPPORTING AND TESTING SMALL CAPTURED MEMBERS

(75) Inventors: Richard R. Hall, Endwell; Candido C. Tiberia, Endicott, both of NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/438,036

(22) Filed: Nov. 10, 1999

(51) Int. Cl.$^7$ .................................................. G01N 3/02
(52) U.S. Cl. .................................................. 73/857
(58) Field of Search ........................ 73/816, 825, 836, 73/837, 840, 856, 857, 798

(56) References Cited

U.S. PATENT DOCUMENTS

| | | |
|---|---|---|
| 2,525,345 * | 10/1950 | Getchell .................... 73/857 |
| 3,335,603 * | 8/1967 | Gram ........................ 73/857 |
| 3,975,950 * | 8/1976 | Erdei ........................ 73/790 |
| 4,537,080 * | 8/1985 | Christiansen .............. 73/857 |
| 4,790,805 | 12/1988 | Slobodkin . |
| 4,852,605 | 8/1989 | Gouhier . |
| 5,033,308 | 7/1991 | Le Compagnon et al. . |
| 5,379,647 | 1/1995 | Sherwin . |
| 5,581,040 * | 12/1996 | Lin ........................... 73/857 |
| 5,633,467 | 5/1997 | Paulson . |
| 5,763,772 | 6/1998 | Bywalez et al. . |
| 5,948,994 * | 9/1999 | Jen et al. .................. 73/856 |

* cited by examiner

*Primary Examiner*—Max Noori
(74) *Attorney, Agent, or Firm*—Salzman & Levy; Lawrence R. Fraley

(57) ABSTRACT

An apparatus for applying a frictionless normal or radial force to a captured member. The apparatus has a fixed fluid bearing and a preloading, axially movable fluid bearing spaced apart from the fixed fluid bearing. A captured member is positioned between the fixed fluid bearing and the movable fluid bearing. A biasing member, disposed adjacent the movable fluid bearing member, biases the movable fluid bearing member against the captured member. The fixed and movable bearings each have oppositely adjacent end surfaces that define a recess for capturing the member therein.

18 Claims, 4 Drawing Sheets

SUBSTANTIALLY FRICTIONLESS BEARING DEVICE FOR SUPPORTING AND TESTING SMALL CAPTURED MEMBERS

FIELD OF THE INVENTION

The present invention relates to load applying devices for applying a low friction load to one or more captured members and, more particularly, to a normal or radial load applying apparatus for testing specimens or components, such as optoelectronic devices and fiber optic connectors.

BACKGROUND OF THE INVENTION

Most mechanical force applying devices that apply a load to a captured member do not provide a purely normal force. Frictional effects influence the force vector, such that the load that is applied usually travels with the surface of the member. Therefore, the load deviates from an ideal normal condition.

The present invention seeks to provide an apparatus for applying a pure normal or radial load. This is accomplished by applying a frictionless, normal or radial force through a fluid (liquid or air) bearing interface disposed at one end of a biasing cylinder and preferably spherically or cylindrically shaped. The bearing interface resembles a ball and socket arrangement in the preferred embodiment. A table fixture comprises four of the biased cylinders. Each cylinder is disposed ninety degrees apart, within a 360 degree radius. The fixture provides a force that simulates a pull force, often applied in a field test to a specimen (e.g., one or more fiber optic cables, a photo detector, or other component or components to be tested).

The specimen is clamped inside the fixture. A load is applied by extending each cylinder, in turn, in serial fashion, while the other cylinders remain retracted about the 360 degree radius of the fixture. No torsional force can be applied by this fixture, owing to the frictionless condition provided by the bearings. The bearings also allow the specimen to deflect in a vertical plane (parallel to the longitudinal axis of rotation).

DISCUSSION OF RELATIVE ART

In U.S. Pat. No. 5,379,647, issued to Sherwin on Jan. 10, 1995 for HOLE ELONGATION TESTING SYSTEM, a device is shown in which a shim is used to reduce friction between two opposing plates.

In U.S. Pat. No. 5,763,772, issued to Bywalez et al on Jun. 9, 1998 for PROCESS FOR DETERMINING THE INITIAL STRESS OF ANTIFRICTION BEARINGS WHICH ARE PRELOADED AGAINST EACH OTHER OR INSTALLED WITH AN INITIAL STRESS, the testing of the deformation of preloaded, anti-friction bearings is illustrated.

In U.S. Pat. No. 5,633,467, issued on May 27, 1997 to Paulson for APPARATUS AND METHOD FOR NON-DESTRUCTIVE TESTING OF STRUCTURES, a low friction support is shown for a probe for testing load bearing of a specimen. The apparatus comprises circumferentially spaced races or bushings.

In U.S. Pat. No. 5,033,308, issued on Jul. 23, 1991 to Le Compagnon et al for METHOD AND APPARATUS FOR TESTING CHARACTERISTICS OF EXTRUDED ELASTOMERIC WEATHERSTRIPS, a frictionless, vertical slide plate is depicted that translates force to a load.

In U.S. Pat. No. 4,790,805, issued to Slobodkin on Dec. 13, 1988 for CONSTRAINT PRESSURE IN LINE-WEB CRUSH-SCORING, a frictionless plunger is shown that applies force to a knife blade.

In U.S. Pat. No. 4,852,605, issued on Aug. 1, 1989 to Gouhier for VALVE OPERATING WITHOUT FRICTION, a frictionless fluid valve is illustrated that uses a membrane deformable by fluid pressure to unseat a valve ball.

In "Pneumatic Pull Tester" by D. G. Pittwood, IBM Technical Disclosure Bulletin, Vol. 13, No. 3 August 1970, pp. 717–718, a pneumatic pull tester is shown with a frictionless piston that can be preloaded.

SUMMARY OF THE INVENTION

In accordance with the present invention, there is provided an apparatus for applying a normal or radial force to a captured member, with a minimum amount of friction. In one embodiment thereof, the apparatus comprises a fixed fluid bearing and a preloading, axially movable fluid bearing spaced apart from the fixed fluid bearing. A spherical/cylindrical captured member is positioned between the fixed fluid bearing and the movable fluid bearing. A biasing member, disposed adjacent the movable fluid bearing member, biases the movable fluid bearing member against the captured member. The fixed and movable bearings each have oppositely adjacent end surfaces that define a recess for capturing the tested member therebetween. The recess surfaces conform to the shape of the captured member, wherein a normal or radial force is applied thereto with a minimum of frictional force. Each of the recess surfaces can comprise a spherical or cylindrical shape or any other regular or irregular shape.

In a second embodiment of the invention, four movably biased fluid bearings, as described above, can be radially positioned at right angles with respect to each other. The four fluid bearings are radially disposed upon a fixture table, defining 360 degrees of arc. The specimen is placed inside a collar disposed in the center of the fixture table. The collar supports the conforming surface of each of the fluid bearings and captures the specimen between the radially disposed surfaces. A normal or radial force is applied to the specimen by a fluid bearing of the fixture table at a given time. The force is applied with a minimum of frictional force, while the other fluid bearings remain movably inactive. Each fluid bearing can apply a normal or radial force to the specimen in a given sequence.

It is an object of this invention to provide a frictionless fluid bearing apparatus for applying a normal or radial force to a machine member.

It is another object of the invention to provide an improved fixture for applying a series of frictionless normal or radial forces to a specimen to be tested.

BRIEF DESCRIPTION OF THE DRAWINGS

A complete understanding of the present invention may be obtained by reference to the accompanying drawings, when considered in conjunction with the subsequent detailed description, in which:

FIG. 1 or FIG. 2 are arranged upon a fixture table whose collar is disposed about the specimen.

For the sake of brevity and clarity, like elements and components will bear the same numbering and designations throughout the figures.

DESCRIPTION OF THE PREFERRED EMBODIMENT

Generally speaking, the invention features an apparatus for applying a frictionless normal or radial force to a member. The apparatus comprises a fixed fluid bearing and a preloading, axially movable, fluid bearing spaced apart from the fixed fluid bearing. A captured member is positioned between the fixed fluid bearing and the movable fluid bearing. A biasing member, disposed adjacent the movable fluid bearing member, biases the movable fluid bearing member against the specimen. The fixed and movable bearings each have oppositely adjacent end surfaces that define a recess for capturing the specimen therein.

Figure 1:
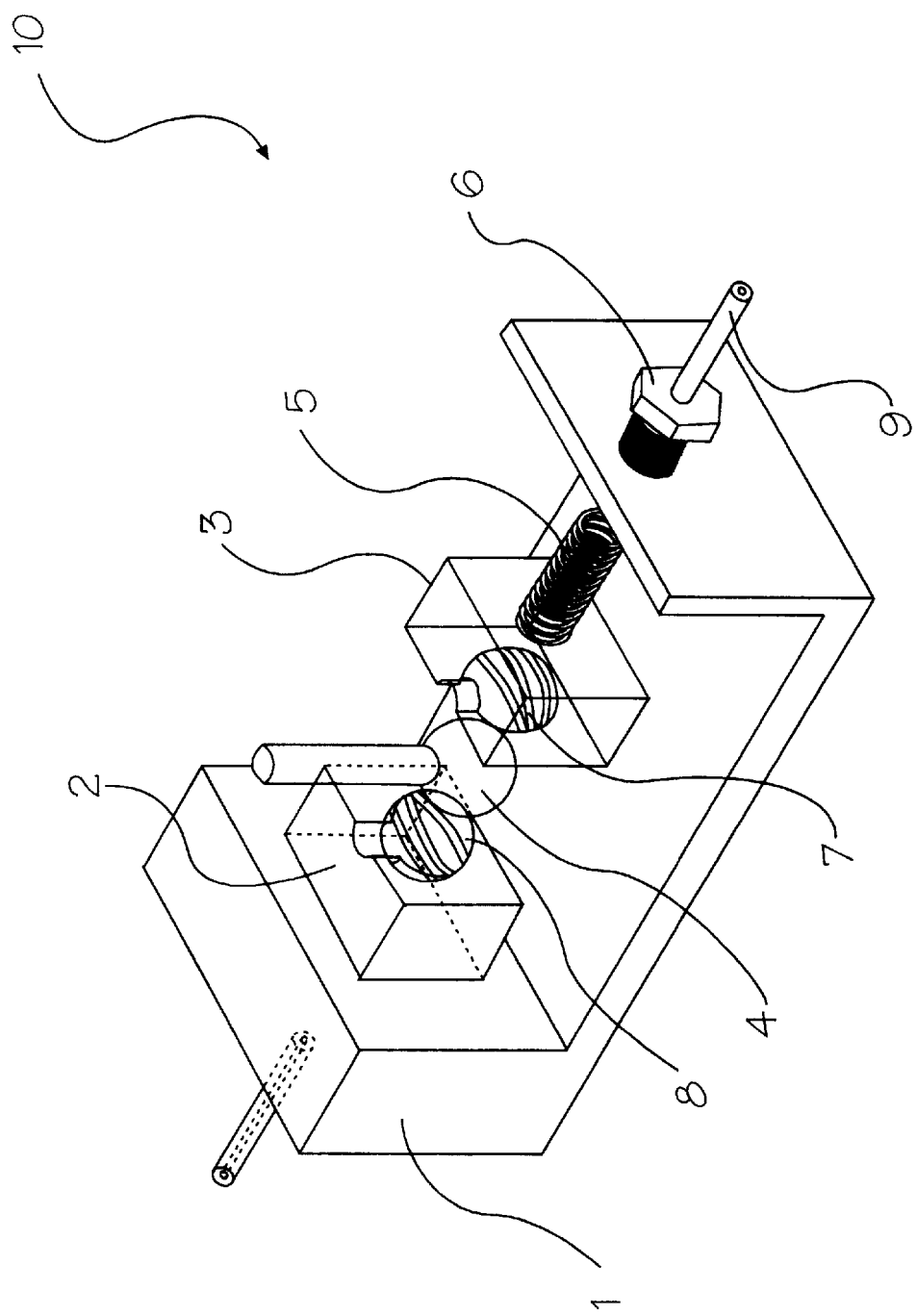
FIG. 1 illustrates a schematic, diagrammatic view of the normal load applying apparatus of this invention, wherein a preloaded bearing has a spherical conforming surface with the specimen.

Now referring to FIG. 1, an apparatus 10 is illustrated for applying a normal or radial force to a captured member or specimen 4 to be tested. It should be understood that the captured member 4 need not be only a specimen to be tested, but could also be one or more machine components or other devices to be contained, processed or handled. As shown in FIG. 1, the captured member 4 is spherically shaped; but other regular and irregular shapes can be used as appropriate for the components (e.g., horizontal and/or vertical split cylinders, plural vertical rods, etc.) being handled. In fact, even particles may be used with this device in molding or particle metallurgy processing. The specimen or guided member 4 is disposed in the apparatus 10 between respective half spherical surfaces 7 and 8, which support and spherically conform to spherically shaped member 4.

The apparatus 10 is defined by a base member 1, carrying a stationary or fixed fluid (gas or liquid) bearing 2 and a preloaded, axially movable, fluid bearing 3, which is spaced apart from the fixed fluid bearing 2, as shown. The components 2 and 3 are shown as solid in FIG. 1, but it should be understood that these may also be adapted to incorporate other physical properties by being heated or cooled or used in conjunction with other fields, such as magnetic, electromagnetic, capacitive, etc. Bearings 2 and 3 can also be segmented. The captured member 4 is positioned between the stationary bearing 2 with its corresponding half spherical surface 8, and the movable bearing 3 and its respective conforming half spherical surface 7.

A coil spring 5, disposed about a rod 9, biases the rod 9 into moving the preloading bearing 3 into contact with the specimen 4, thus capturing the specimen 4 between the respective conforming half spherical surfaces 7 and 8. An adjustment nut or collar 6 adjusts the spring force upon the rod 9. The bearings 2 and 3 allow a normal or radial force to be exerted upon the spherical specimen 4 with a minimum of frictional force.

Figure 2:
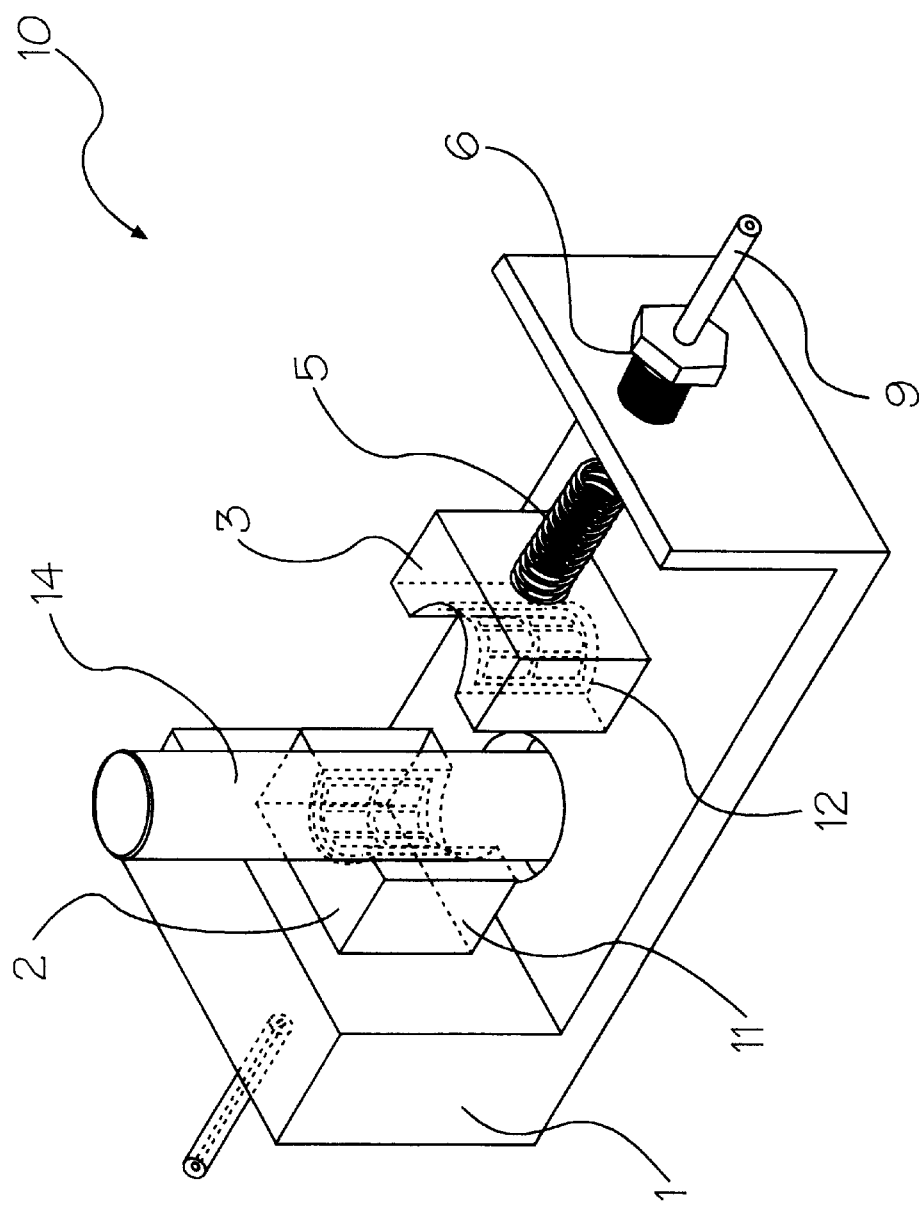
FIG. 2 depicts a schematic, diagrammatic view of the normal load applying apparatus of FIG. 1, wherein the preloaded bearing has a cylindrical conforming surface with the specimen.

Referring to FIG. 2, the apparatus 10 is now modified with cylindrical surfaces 11 and 12, respectively, in order to conform to, and capture, a cylindrically shaped specimen 14.

Figure 3:
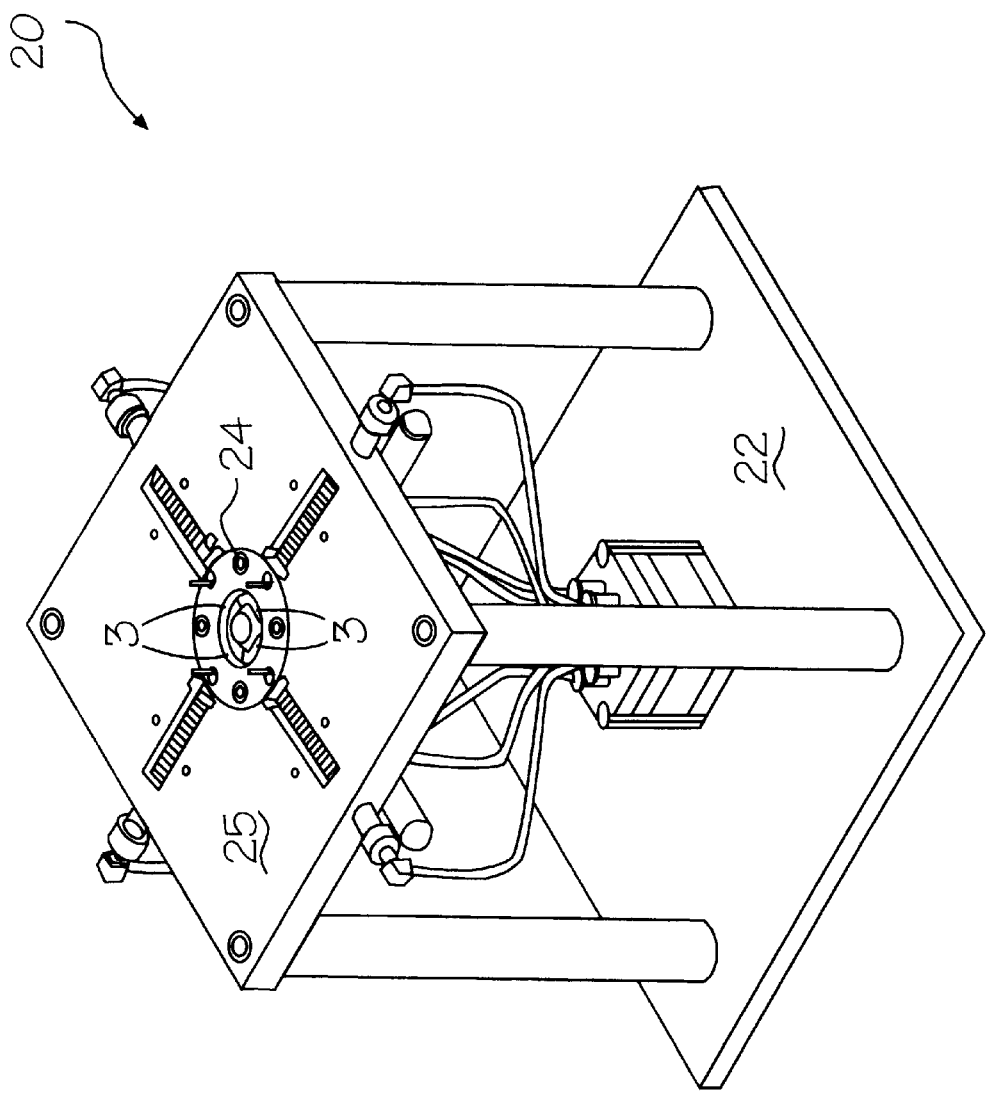
FIG. 3 shows a perspective view of another embodiment of this invention, wherein the apparatuses of either

Referring to FIG. 3, another embodiment 20 of this invention is illustrated. The embodiment 20 comprises a fixture table 22, upon which four movable fluid bearings 3 are disposed within a collar 24 disposed upon table top 25. A rod and spring mechanism for biasing each bearing 3, as defined by rod 9, spring 5 and adjustment nut 6, illustrated in FIG. 1, is used to move each respective bearing 3 and its conforming surface into operative engagement with the specimen (not shown).

The collar 24 supports the conforming surface of each of the bearings 3, and captures the member between these radially disposed surfaces. A normal or radial force is applied to the specimen by one bearing 3 at a given time. The force is applied with a minimum of frictional force, while the other bearings 3 remain movably inactive. Each bearing 3 can apply a normal or radial force to the specimen in a given sequence.

It may also be possible to use three movable air bearings 3 upon table top 25, each being 120 degrees apart. The number of bearings 3 can be increased to any practical number to effect a more balanced and distributed force system.

Figure 4:
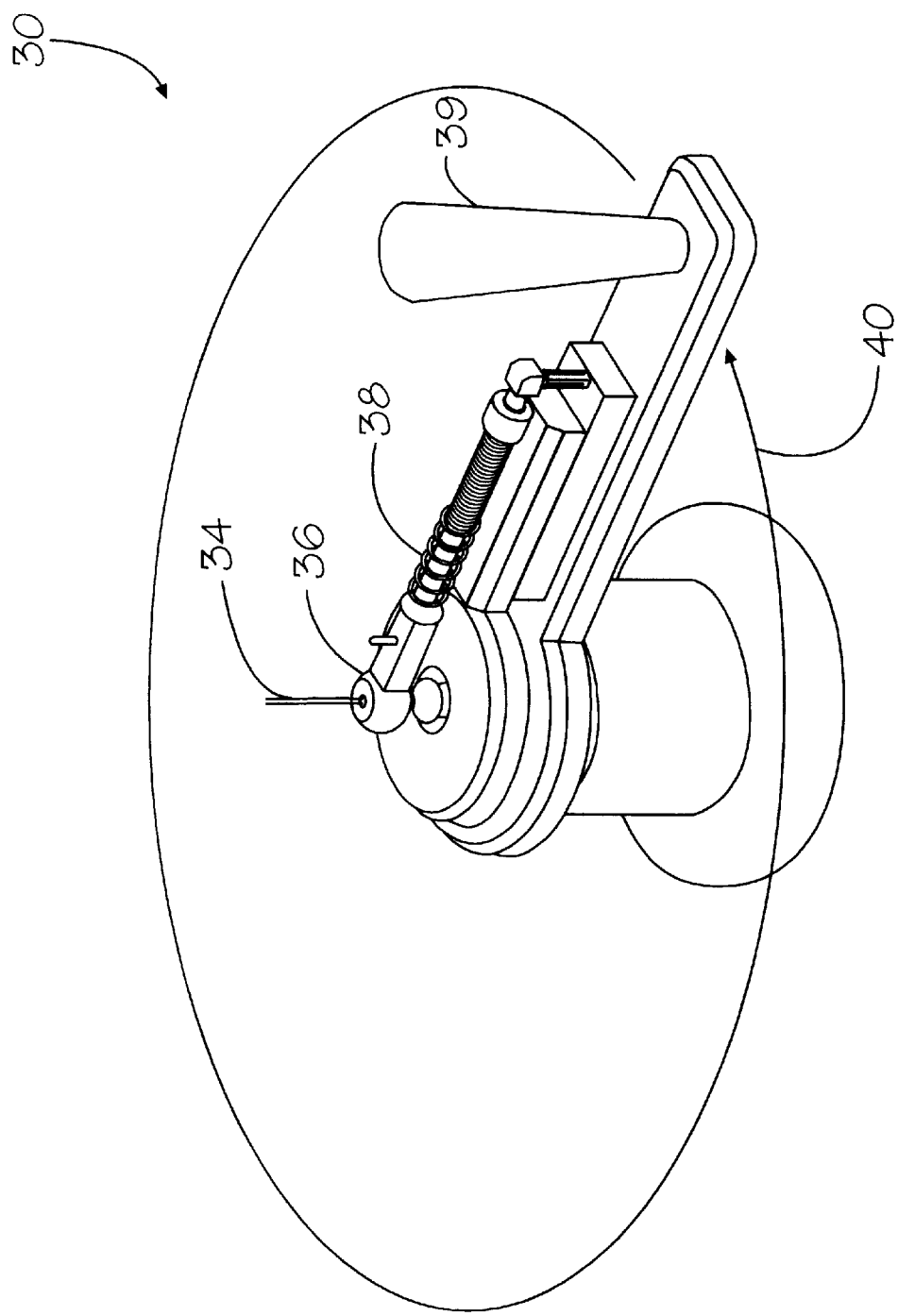
FIG. 4 shows a perspective view of yet another embodiment of the invention in which a sole, unbalanced force is applied to the periphery of a component to be handled.

Referring now to FIG. 4, there is shown a single, unbalanced configuration 30. The captured member 34, in this case an optical fiber, is surrounded by a single fluid bearing 36 to which is attached a preload spring 38. A manual handle 39 is provided to rotate the force-applying mechanism completely around the captured member 34, as shown by arrow 40. Of course, automating this single load-applying device 30 is well within the scope of the invention.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. An apparatus for applying a normal, or radial force to a small, fragile specimen, whose weight is in fractions of a gram, and is under test, said apparatus applying said normal, or radial force with a minimum amount of friction, said apparatus comprising:

a base for supporting a stationary and movable fluid bearing, respectively;

a fixed fluid bearing supported by said base;

a preloading, axially movable, fluid bearing spaced apart from said stationary fluid bearing, and supported upon said base;

an interface member carried by each fluid bearing that comprises a conforming surface to a small, fragile specimen under test, said specimen weighing fractions of a gram, and being positioned between each respective interface member; and a biasing member disposed adjacent said movable fluid bearing, for biasing said interface member of said movable fluid bearing against the specimen, thus capturing, and applying a normal or radial force against the specimen with a minimum of friction, whereby said specimen is both supported and subjected to a load by the fluid disposed between the fluid bearings.

2. The apparatus for applying a normal or radial force to a captured member in accordance with claim 1, further comprising adjustment means supported by said base for adjusting the normal or radial force being exerted upon said at least one captured member by said movable, fluid bearing.

3. The apparatus for applying a normal or radial force to a captured member in accordance with claim 1, wherein each interface member comprises a curved surface.

4. An apparatus for applying a normal or radial force to a captured member with a minimum amount of friction, said apparatus comprising:

a base for supporting a stationary and movable fluid bearing, respectively;

a stationary fluid bearing supported by said base;

a plurality of preloading, axially movable fluid bearings spaced apart from one another and from said stationary fluid bearing and supported upon said base;

an interface member carried by each of said fluid bearings that comprises a surface conforming to a captured member under test, said captured member being positioned between respective interface members;

biasing members disposed adjacent said respective movable fluid bearings for biasing said interface member of said movable fluid bearings against said captured member, thus capturing and applying a normal or radial force against said captured member with a minimum of friction; and adjustment means supported by said base, for adjusting the normal or radial force being exerted upon said captured member by said movable fluid bearing, whereby said captured member is both supported and subjected to a load by the fluid disposed between the fluid bearings.

5. The apparatus for applying a normal or radial force to a captured member in accordance with claim 4, wherein each interface member comprises a substantially spherical surface.

6. The apparatus for applying a normal or radial force to a captured member in accordance with claim 4, wherein each interface member comprises a substantially cylindrical surface.

7. An apparatus for applying a normal or radial force to a captured member with a minimum amount of friction, said apparatus comprising:

a table for supporting a plurality of substantially equally spaced apart, movable fluid bearings;

a plurality of spaced apart, axially movable fluid bearings supported upon said table;

an interface member carried by each of said fluid bearings, said interface members each comprising a surface conforming to a captured member, said captured member being positioned between each of said respective interface members; and a biasing member disposed adjacent said movable fluid bearing, for biasing each interface member of said movable fluid bearing against said captured member, thus capturing and applying a normal or radial force against said captured member with a minimum of friction, whereby said captured member is both supported and subjected to a load by the fluid disposed between the fluid bearings.

8. The apparatus for applying a normal or radial force to a captured member in accordance with claim 7, further comprising adjustment means supported by each fluid bearing for adjusting the normal or radial force.

9. The apparatus for applying a normal or radial force to a captured member in accordance with claim 7, wherein only one fluid bearing is movable at one time, with the other fluid bearings remaining immobile.

10. The apparatus for applying a normal or radial force to a captured member in accordance with claim 7, wherein each fluid bearing is movable in sequence.

11. The apparatus for applying a normal or radial force to a captured member in accordance with claim 7, wherein each interface member comprises a substantially spherical surface.

12. The apparatus for applying a normal or radial force to a captured member in accordance with claim 7, further comprising a collar disposed upon said table, said collar supporting each interface member about said captured member.

13. The apparatus for applying a normal or radial force to a captured member in accordance with claim 1, wherein at least one of said interface members comprises means for transferring a physical property to said at least one captured member.

14. An apparatus for applying a radial force to at least one captured member, said apparatus comprising:

a base for supporting a movable fluid bearing;

a preloading fluid bearing radially movable 360 degrees with respect to at least one captured member;

an interface member carried by said fluid bearing comprising a collar for surrounding said at least one captured member; and a biasing member disposed adjacent said fluid bearing for biasing said interface member of said fluid bearing against said at least one captured member, to facilitate applying a force radially against said at least one captured member as said fluid bearing is rotated therearound.

15. A method for handling a component comprising:

both supporting and applying a force to a component via a fluid carried by a load applying device;

providing a base on which is mounted a component to be handled and a load-applying device, said load applying device comprising an interface member having a surface conforming to said component; and biasing said load-applying device against said component to apply a radial or normal force thereto, via said fluid.

16. The method for handling a component in accordance with claim 15, wherein said biasing step comprises moving one of a predetermined number of fluid bearings, while each of said remaining fluid bearings remains immobile.

17. The method for handling a component in accordance with claim 15, wherein said fluid bearings are movable in sequence.

18. The method for handling a component in accordance with claim 15, wherein said load-applying device surrounds said component and said biasing step comprises rotating said load-applying device up to 360 degrees with respect to said component.

* * * * *